United States Patent
Uhland et al.

(10) Patent No.: US 8,388,569 B2
(45) Date of Patent: *Mar. 5, 2013

(54) DELIVERY DEVICES AND METHODS WITH COLLIMATED GAS STREAM AND PARTICLE SOURCE

(75) Inventors: Scott Uhland, San Jose, CA (US); Eric Peeters, Mountain View, CA (US)

(73) Assignee: Xerox Corporation, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/089,769

(22) Filed: Apr. 19, 2011

(65) Prior Publication Data

US 2012/0271221 A1   Oct. 25, 2012

(51) Int. Cl.
  *A61M 37/00*   (2006.01)
(52) U.S. Cl. .......... 604/24; 604/23; 604/25; 604/26; 604/58; 604/68; 604/69; 604/70; 604/140; 604/145; 604/146
(58) Field of Classification Search .......... 604/23–26, 604/58, 68–70, 140, 145–148
See application file for complete search history.

(56) References Cited

U.S. PATENT DOCUMENTS

| | | | |
|---|---|---|---|
| 4,286,592 A * | 9/1981 | Chandrasekaran | 424/448 |
| 5,630,796 A | 5/1997 | Bellhouse et al. | |
| 5,865,796 A * | 2/1999 | McCabe | 604/71 |
| 5,899,880 A | 5/1999 | Bellhouse et al. | |
| 5,947,928 A | 9/1999 | Muller | |
| 6,116,718 A | 9/2000 | Peeters et al. | |
| 6,475,181 B1 | 11/2002 | Potter et al. | |
| 6,592,545 B1 | 7/2003 | Bellhouse et al. | |
| 6,641,553 B1 * | 11/2003 | Chee et al. | 604/68 |
| 6,881,200 B2 | 4/2005 | Bellhouse et al. | |
| 6,893,664 B1 | 5/2005 | Burkoth et al. | |
| 7,207,967 B1 * | 4/2007 | Bellhouse et al. | 604/70 |
| 7,547,292 B2 | 6/2009 | Sheldrake et al. | |
| 7,618,394 B2 | 11/2009 | Bellhouse et al. | |

(Continued)

FOREIGN PATENT DOCUMENTS

| | | |
|---|---|---|
| CA | 2259194 A1 | 1/1998 |
| EP | 1508379 A1 * | 2/2005 |
| WO | 00/62846 A1 | 10/2000 |
| WO | 02/055139 A1 | 7/2002 |

OTHER PUBLICATIONS

European Search Report of Application No. 2164304.3 dated Jul. 18, 2012.

*Primary Examiner* — Bhisma Mehta
*Assistant Examiner* — Larry R Wilson
(74) *Attorney, Agent, or Firm* — Sutherland Asbill & Brennan LLP

(57) ABSTRACT

Delivery devices, methods and systems are provided for the delivery of particles into a biological tissue. The device includes a gas source comprising a gas or capable of selectively producing a gas; a first particle source comprising a first plurality of particles; a first collimator fluidly connected with the gas source and adapted to form a collimated stream of the first plurality of particles entrained in the gas. The device also includes a tissue-interfacing surface adapted to interface with a surface of the tissue and orient the first collimator with the tissue such that the collimated stream of the first plurality of particles will penetrate the tissue in a direction substantially perpendicular to the surface of the tissue.

20 Claims, 7 Drawing Sheets

U.S. PATENT DOCUMENTS

| | | | |
|---|---|---|---|
| 7,727,223 B2 * | 6/2010 | Potter et al. | 604/506 |
| 2002/0065533 A1 * | 5/2002 | Weaver et al. | 606/191 |
| 2004/0204700 A1 | 10/2004 | Weaver et al. | |
| 2004/0215135 A1 | 10/2004 | Sheldrake et al. | |
| 2008/0300535 A1 | 12/2008 | Kendall et al. | |
| 2010/0121262 A1 | 5/2010 | Bates et al. | |

* cited by examiner

DELIVERY DEVICES AND METHODS WITH COLLIMATED GAS STREAM AND PARTICLE SOURCE

FIELD

The present disclosure is generally in the field of the administration of substances, such as drugs, into a biological tissue, and in certain embodiments more particularly relates to devices and methods for the transdermal delivery of a drug to a patient.

BACKGROUND

Transdermal drug delivery is an area of interest, particularly as an alternative to drug delivery via needle injection. Examples of transdermal drug delivery include the use of transdermal patches to facilitate the diffusion of a drug into the skin.

The stratum corneum provides the most significant barrier to diffusion of a topically applied drug into the body of a patient. The stratum corneum is the top layer of the skin and varies in thickness from approximately ten to several hundred micrometers, depending on the region of the body. It is composed of layers of dead, flattened keratinocytes surrounded by a lipid matrix, which together act as a brick-and-mortar system that is difficult to penetrate.

Most transdermal drug delivery applications utilize at least one of two main pathways by which drugs can cross the skin and reach the systemic circulation. Using the "transcellular pathway" drugs cross the skin by directly passing through both the phospholipids membranes and the cytoplasm of the dead keratinocytes that constitute the stratum corneum. Although this is the path of shortest distance, the drugs encounter significant resistance to permeation. Using the "intercellular pathway" drug passes through the small spaces between the cells of the skin, making the route more tortuous. Although the thickness of the stratum corneum is only about 20 μm, the actual diffusional path of most molecules crossing the skin is on the order of 400 μm. The 20-fold increase in the actual path of permeating molecules greatly reduces the rate of drug penetration.

Another transdermal drug delivery approach utilizes high velocity jets to impart sufficient momentum to a drug form to cause the drug form to breach the stratum corneum. Most commonly high velocity jet injectors are liquid-based. Liquid-based high velocity jet injectors produce liquid jets composed of liquid solutions or colloidal suspensions of drug macromolecules to deliver the drug to the patient. The liquid jet velocity may be in the range of 100 m/s to 150 m/s. The use of liquid-based high velocity injectors has not achieved wide acceptance due to various challenges including: splashing, which risks contamination and results in drug waste; pain and bruising due to lack of control over liquid penetration; high energy requirements; slow delivery rates; usability challenges and operational skill requirements, which militate against the high reproducibility required of a drug delivery device; and formulation challenges caused by jetting constraints such as viscosity and surface tension.

Accordingly, it would be desirable to provide new methods, devices, and systems for delivering drugs to patients.

SUMMARY

In one aspect, a delivery device is provided for the delivery of particles into a biological tissue. The device includes a gas source comprising a gas or capable of selectively producing a gas; a first particle source comprising a first plurality of particles; a first collimator fluidly connected with the gas source and adapted to form a collimated stream of the first plurality of particles entrained in the gas. The device also includes a tissue-interfacing surface adapted to interface with a surface of the tissue and orient the first collimator with the tissue such that the collimated stream of the first plurality of particles will penetrate the tissue in a direction substantially perpendicular to the surface of the tissue.

In another aspect, a method is provided for delivering particles into a biological tissue. The method includes delivering a pressurized gas into a collimator to produce a stream of gas; and then releasing a first plurality of particles into the stream of gas to produce a collimated stream of the first plurality of the particles entrained in the gas. The method further includes delivering the first plurality of particles through a surface of the tissue in a direction substantially perpendicular to the surface of the tissue.

In yet another aspect, a drug delivery system is provided for delivering a drug into a biological tissue. The system includes a particle delivery device for the delivery of particles into a tissue that includes a gas source comprising a gas; a first particle source comprising a first plurality of particles; a first collimator fluidly connected with the gas source and adapted to form a collimated stream of the first plurality of particles entrained in the gas; and a tissue-interfacing surface adapted to interface with a surface of the tissue and align the first collimator with the tissue such that the collimated stream of the first plurality of particles will penetrate the tissue in a direction substantially perpendicular to the surface of the tissue. The system also includes a drug-delivery patch comprising a drug-permeable tissue-interfacing surface, a drug-impermeable backing layer, and a drug contained between the tissue-interfacing surface and the backing layer.

DETAILED DESCRIPTION

Figure 1:
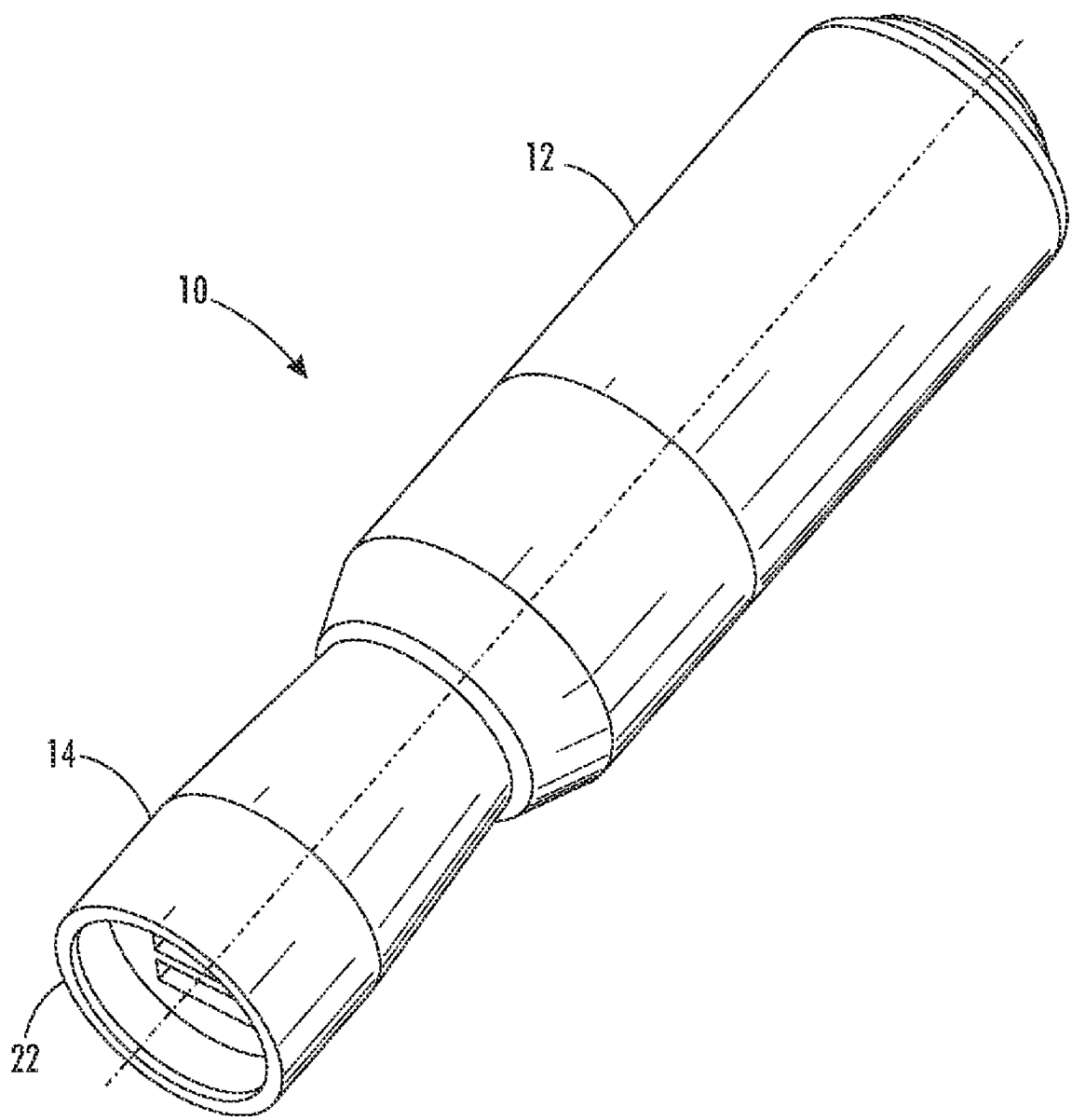
FIG. 1 is a perspective view, illustrating a drug delivery device in accordance with one or more embodiments of the present disclosure.
Figure 2:
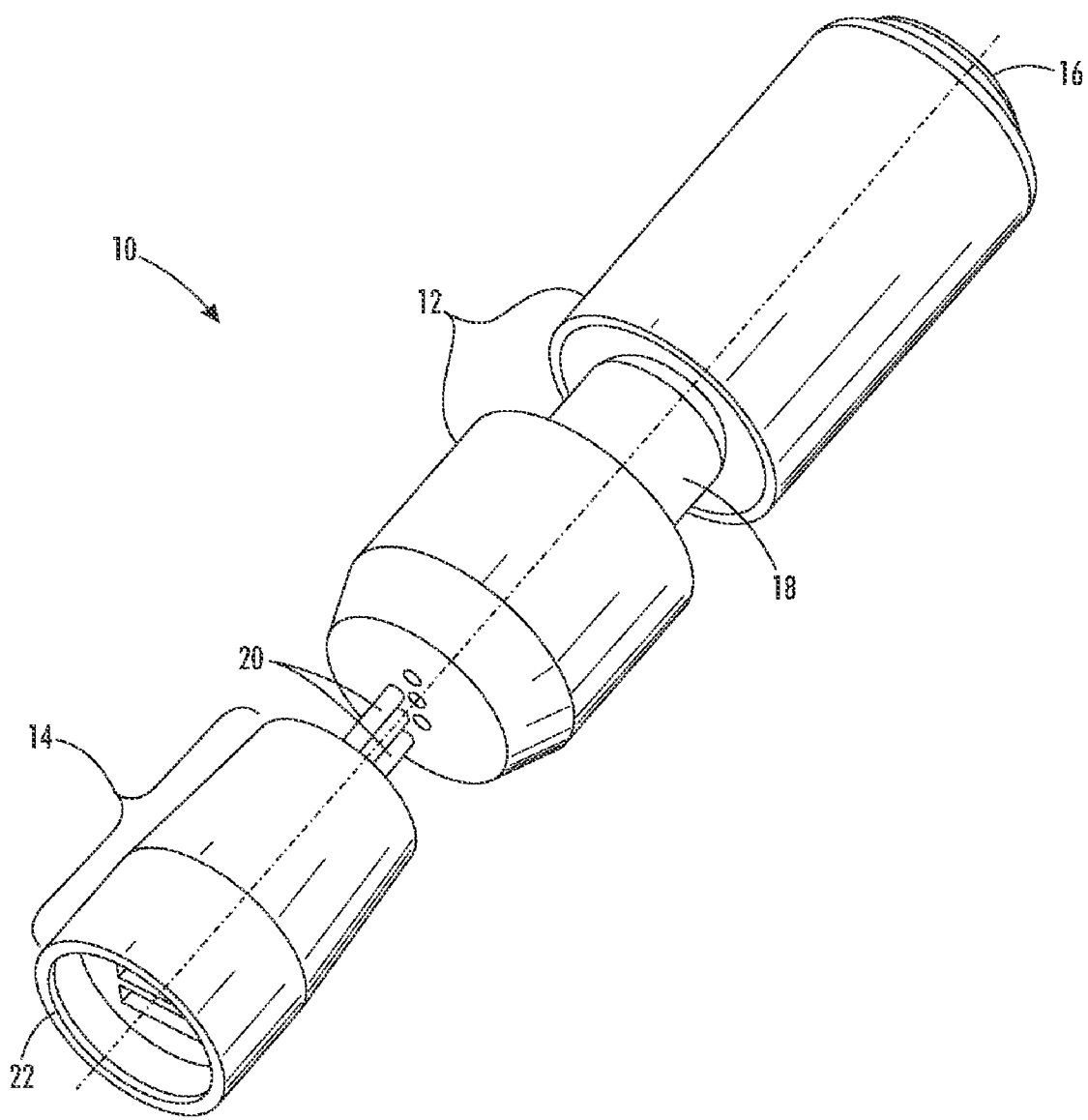
FIG. 2 is an exploded perspective view, illustrating a drug delivery device in accordance with one or more embodiments of the present disclosure.

New devices, methods, and systems are provided for the delivery drugs and other types of particles into tissue. In some embodiments, drug or particle delivery is achieved by directing a plurality of collimated gas streams at a tissue to form pores in the tissue to allow for the passage of the drug or other particle therethrough, such as for local or systemic drug delivery. The collimation of the drug particles advantageously enables excellent control of the x, y, and z distribution/penetration of the substances, thereby beneficially providing no/minimal pain and tunable and uniform drug particle momentum. In certain embodiments, the pores are formed by the momentum of the gas molecules in the collimated gas stream striking the tissue. Poration of the tissue may be enhanced by collisions of drug or other particles against the tissue, thereby allowing the drug or other particles to penetrate the surface, or outer layers, of the tissue.

Devices, methods, and systems are further provided for producing supersonic collimated particle streams that maintain a beam diameter of less than about 100 µm or less than about 50 µm over a length of about 1 cm or more. Advantageously, in some embodiments, such devices methods reduce or eliminate recoil/splashing, pain, and bruising associated with other needleless injection techniques. Such devices, methods, and systems, in some embodiments, also provide increased control and reliability of drug delivery and reduce the operational skill required to perform needleless drug injection. This, in turn, advantageously can promote more precise and accurate drug dosing.

The devices, systems, and methods described herein may be used for targeted delivery of therapeutic, diagnostic, or other substances into or through a variety of types of tissues or biological barriers, including suitable cells, tissues, or organs, including the skin or parts thereof, mucosal tissues, vascular tissues, lymphatic tissues, and the like. In other embodiments, the target cells or tissues may be in various animals, plants, insects, or other organisms. The tissue may be in humans or other mammals. For instance, a drug or other substance may be delivered through the stratum corneum, and into underlying dermal tissues. The tissue may be a biological tissue of a patient in need of a drug. The patient may be a human, cattle, sheep, horse, pig, dog, cat, or other mammal, for example.

The devices and methods described herein may further include one or more of the device features and techniques described in U.S. patent application Ser. No. 13/089,777, entitled "Drug Delivery Devices and Methods with Collimated Gas Stream and Release-Activatable Tape" and in U.S. patent application Ser. No. 13/089,783, entitled "Delivery Devices and Methods with Collimated Gas Stream and Drug Reservoir," which are filed concurrently herewith and which are incorporated by reference in their entirety.

I. Drug Delivery Devices

Drug delivery devices, such as for transdermal drug delivery, are disclosed. In one aspect, the drug delivery device includes a gas source which contains or produces a pressurized gas. The drug delivery device also includes one or more collimators that are fluidly connected with the gas source. Each of the collimators may be adapted to form a plurality of collimated gas streams comprising the gas. The device may further include a skin interfacing surface that is adapted to mate with the skin (or other tissue surface) and align the collimator with the skin such that the plurality of collimated gas streams penetrate the skin in a direction substantially perpendicular to the skin.

In another aspect, a drug delivery device is provided that includes a drug reservoir containing a drug in solid particle or liquid form, a gas source for storing or producing a pressurized gas, and a collimator comprising a plurality of conduits. Each of the plurality of conduits may include an inlet, an outlet and a drug port between the inlet and the outlet. Each drug port is fluidly connected (or is operable to become fluidly connected) with the drug reservoir, and the inlet end of each of the plurality of conduits is fluidly connected (or is operable to become fluidly connected) with the gas source.

In certain embodiments, the drug delivery device is configured to produce collimated gas streams having a sufficient velocity to penetrate human stratum corneum. For example, the drug delivery device may be configured to produce collimated gas streams having a velocity of about 100 to about 1500 m/s. In certain embodiments, each of the collimated gas streams has a diameter of about 5 µm to about 500 µm at a distance of about 0.5 mm to 10 mm from the outlet of the collimator.

Effective collimation may be achieved by delivering a propellant into a conduit and controllably introducing or metering the particles into the channel such that the propellant propels the particles into the barrier. The shape of the channel or conduit may result in a collimated (i.e., focused) flight of the propellant and particles to the barrier. The particles may then be introduced into the propellant stream from one or more material inlet ports. The propellant may enter the channel at a high velocity. Alternatively, the propellant may be introduced into the channel at a high pressure, and the channel may include a constriction (e.g., de Laval or other converging/diverging type nozzle) for converting the high pressure of the propellant to high velocity. In such a case, the propellant is introduced at a port located at a proximal end of the channel (i.e., near the converging region), and the material ports are provided near the distal end of the channel (at or further down-stream of a region defined as the diverging region), allowing for introduction of material into the propellant stream. It has been demonstrated that a propellant and the material flow pattern can remain relatively collimated for a distance of up to 10 millimeters. For example, the stream does not deviate by more than about 20 percent, and preferably by not more than about 10 percent, from the width of the exit orifice for a distance of at least 4 times the exit orifice width.

In certain embodiments, the collimator may include a plurality of conduits. Each conduit may have an inlet and an outlet. Each of the conduits may have a venturi located between the inlet and the outlet. In certain embodiments, each conduit has an expansion neck region which expands the gas stream downstream of the inlet. For example, an expansion neck region may be provided at the exit of the venturi.

In some embodiments, the drug delivery device releases a drug from the drug source into the collimated gas streams such that the drug becomes entrained in each gas stream and is transported into the skin in a direction substantially perpendicular to the skin. For example, each of the conduits may have a drug port (i.e., an opening) between the inlet and outlet of the conduit, and the drug port may be fluidly connected with the drug source. In certain embodiments, the drug port is downstream of the venturi. In some embodiments, the drug delivery device includes a rupturable membrane between the drug source and the collimator. For example, the rupturable membrane may seal the drug port until the membrane is ruptured. Rupture of the rupturable membrane may be controlled by the operator of the device.

When the material port is placed downstream of the venturi or downstream of the location at which the high velocity stream of gas is established, the particles may be pushed into the high velocity gas stream by a pressure differential (e.g., Bernoulli's force). For example, based on Bernoulli's equation, if particles are contained in an open reservoir adjacent to a high velocity gas stream of 750 m/s, a pressure difference of about 2.2 atm is generated and pushes the particles into the gas stream.

The drug delivery device may include a standoff between the collimator and the skin interfacing surface such that a gap is provided between the outlets of the collimator and the skin when the skin interfacing surface is placed against the skin. For example, the standoff may create a gap of about 0.5 to about 10 mm.

In some embodiments, the collimator and drug source are provided in the form of a removable cartridge. The drug delivery device may include one or more cartridge receivers for receiving one or more removable cartridges. The cartridge may be inserted into the receiver for delivering drugs contained in the cartridge into a patient's skin. The cartridge, which may be depleted of drug, may thereafter be removed and replaced. In some embodiments, the drug delivery device includes a plurality of cartridge receivers for receiving multiple cartridges. In certain embodiments, each cartridge may contain an amount of the drug suitable for an individual dosage.

An exemplary embodiment of a drug delivery device 10 is illustrated in FIGS. 1-3. The drug delivery device 10 includes a gas source housing 12 and a cartridge housing 14. The gas source housing 12 may be dimensioned to fit comfortably in a hand when the fingers are wrapped around the cylindrical sidewall of the gas source housing 12. The cartridge housing 14 is located at one end of the drug delivery device 10. As illustrated in FIG. 2, the cartridge housing 14 may be located at the end of the drug delivery device 10 opposite a push switch 16. Although the push switch 16 is illustrated at one end of the drug delivery device 10, the push switch 16 can also be located elsewhere on the device, such as on the cylindrical sidewall of the gas source housing 12. The cartridge housing 14 includes at one end a tissue interfacing surface 22. The tissue interfacing surface 22 may be a generally planar surface that is adapted to align the gas streams in a substantially perpendicular direction to the tissue surface mating with the tissue interfacing surface 22.

As illustrated in FIG. 3, the gas source housing 12 also surrounds a gas source 18, which contains or generates a pressurized gas. In the embodiment of FIG. 3, the pressurized gas is selectively delivered to one of three cartridges 34 via a corresponding gas delivery conduit 20. Gas delivery may be actuated by pressing the push switch 16. A power source 32 and a controller 33 may then selectively actuate a valve to control the flow of pressurized gas from the gas source 18 through the desired gas delivery conduit 20. For example, the controller 33 may sequentially activate one of three control valves with each press of the push switch 16. In embodiments in which gas is generated on-board the drug delivery device 10, the controller 33 may also actuate the process that generates the gas.

The cartridge housing 14 includes three cartridge receivers for receiving the three cartridges 34. The cartridges 34 may be removable and replaceable, such that the new cartridges can be inserted into the cartridge receivers once the original cartridges 34 are expended. To this end, the cartridge housing 14 may comprise cartridge removal devices, e.g., spring-loaded push rods, to facilitate the removal of expended cartridges from the cartridge housing 14. Although slots for three cartridges 34 is illustrated in the present embodiment, it should be noted that the device could be designed to accommodate one, two, four, or any number of cartridges 34. The cartridge housing 14 includes a standoff 36 which provides a gap of distance x between the end of the cartridges 34 and tissue interfacing surface 22. In some embodiments, the distance x of the gap may between about 0.1 and about 5 mm.

Gas Source

The device may include a gas source which contains or produces a pressurized gas. For example, gas pressures greater than or equal to about 0.5 MPa would be sufficient entrain and drive the collimated gas/drug from the drug delivery device. The pressurized gas may be various gases, including, but not limited to air, carbon dioxide, nitrogen, or oxygen. In some embodiments, pressure is generated on-board. For example, gas may be generated on-board by a chemical or electro-chemical reaction. One example of such a system includes an electrochemical cell that breaks down water into hydrogen gas ($H_2$) and oxygen gas ($O_2$). The water source could be in liquid form or stored in a hydrogel on-board the device. Another example is a system that relies on phase transformation, such as boiling of water to generate steam. Still other examples include systems that utilizes a chemical reaction or decomposition, for instance, sodium azide decomposition into sodium and nitrogen gas ($N_2$) or the reaction of calcium carbonate with an acid to yield carbon dioxide gas ($CO_2$). In some embodiments, the gas is provided in a pressurized vessel and is delivered, such as through a valve, to the collimator when needed. For example, the valve may be actuated by pressing a push switch on the drug delivery device. In some embodiments, the pressure may be generated by a mechanical device, such as a pump.

Collimator

The device may include a collimator for producing a plurality of discrete collimated gas streams. The term "collimated" as used herein refers to a stream of gas, which may include solid particles or liquid entrained therein, that maintains a well-defined and substantially constant diameter over a desired, useful distance, including when unconstrained by a sidewall structure. For example, the collimator may maintain a diameter of about 5 μm to about 500 μm over a distance of about 0.5 mm to about 10 mm. The collimator and drug delivery device may be configured and arranged to produce gas streams having a velocity of about 100 to about 1500 m/s.

An exemplary collimator 40 is illustrated in FIG. 4. The collimator 40 includes a plurality of conduits, which may be etched, cut or milled on the surface of a plate. Although the conduits are illustrated as open channels in FIG. 4, it should be appreciated that the channels are bounded by a top layer when used. The top layer may be integral with the cartridge 34 or it may be a surface of the cartridge receiver that mates with the collimator 40 when the cartridge 34 is received in the cartridge receiver. Each of the conduits has an inlet 44 at one end of the cartridge 34 and an outlet 46 at the other end of the cartridge 34. A venturi 48 is provided in each conduit between the inlet 44 and the outlet 46. An expanding neck region 50 is provided immediately downstream of each venturi 48. As the pressurized gas passes through the venturi 48, expands into the expanding neck region 50, and exits through outlet 46 well-defined, collimated gas streams are formed. The venturi is designed so as to produce an exit pressure of approximately 1 atmosphere, i.e. the pressure inside the free jet is substantially equal to atmosphere, so as to not produce an expanding or contracting jet. A drug port 52 is provided downstream of the venturi 48 for releasing a drug from drug source 42 and entraining the drug in the gas stream.

Although the collimator 40 has been described with reference to drug delivery, it should be noted that the collimator may be used to deliver other liquids or particles into a tissue as is described in greater detail subsequently.

Drug/Particle Source

Drugs or other particles may be provided on-board the drug delivery device in a drug or particle source. In some embodiments, the drugs or particles are contained in a reservoir. As previously described, a drug port may be provided between the drug source and the collimator for allowing release of the drug therethrough.

Release of the drug may be controlled by a rupturable membrane that seals the drug port. The rupturable membrane may be ruptured by the pressure change caused by the pressurized gas being fed through the collimator. Alternatively, the rupturable membrane may be ruptured by actuation of another element. For example, the rupturable membrane may be ruptured by electrothermal ablation, mechanical puncturing (e.g., with a scepter), heating (e.g., melting the membrane), chemical reaction, or volumetric expansion of the reservoir contents Other release devices may be provided to control the release of the drug from the drug reservoir. For example, an electric charge or movable cover may be used to prevent the release of the drug through the drug port until such later time that release is desired and the release device is actuated.

In other embodiments, the drug may be released from a release-activatable tape. For example, the release-activatable tape may have the drug disposed on the tape. In some embodiments, the release-activatable tape may be used to release other types of solid particles or liquids. The release-activatable tape may comprise a UV-sensitive, heat-sensitive, or electrical-sensitive material. The device may also include a controller that is adapted to actuate the release of the drug or other particle from the release-activatable tape. In some embodiments, the controller is adapted to actuate the release of the drug from the release-activatable tape after the pressurized gas has begun to pass through the collimator.

Figure 6:
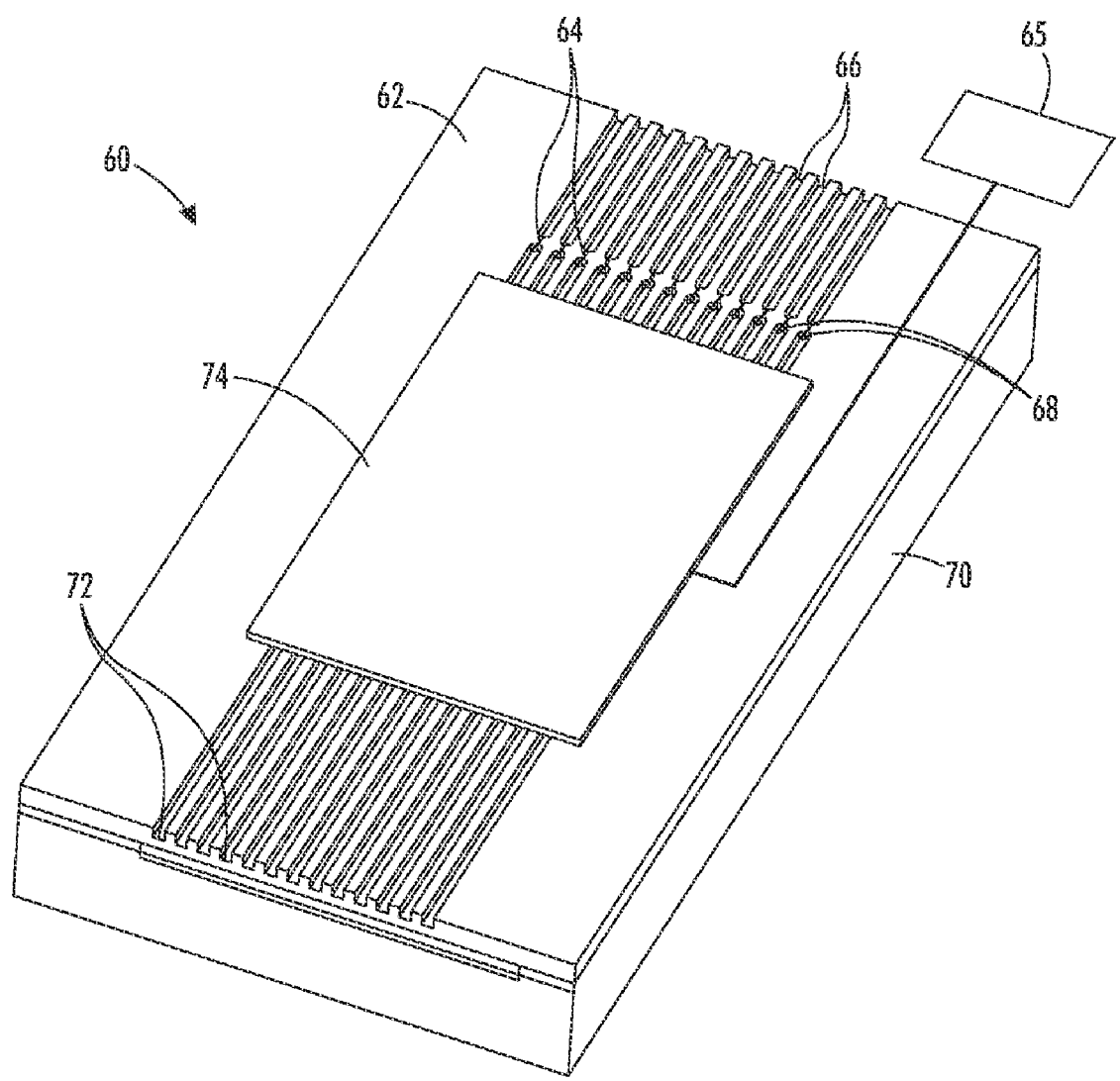
FIG. 6 is a detail view, illustrating a cartridge for a drug delivery device and a particle-release tape in accordance with one or more embodiments of the present disclosure.

In some embodiments, the release-activatable tape is positioned within or adjacent to the first collimator. For example, as illustrated in FIG. 6, the cartridge 60 may include a collimator 62 having a plurality of conduits or channels, which may be etched, cut or milled on the surface of a plate. Although the conduits are illustrated as open channels in FIG. 6, it should be appreciated that the channels are bounded by a top layer when used. The top layer may be integral with the cartridge 60. Each of the conduits has an inlet 66 at one end of the cartridge 60 and an outlet 72 at the other end of the cartridge 60. A venturi 64 is provided in each conduit between the inlet 66 and the outlet 72. An expanding neck region 68 is provided immediately downstream of each venturi 64. As the pressurized gas passes through the venturi 64, expands into the expanding neck region 68, and exits through outlet 72 well-defined, collimated gas streams are formed. The venturi is designed so as to produce an exit pressure of approximately 1 atmosphere, i.e. the pressure inside the free jet is substantially equal to atmosphere, so as to not produce an expanding or contracting jet. A particle-release tape 74 is provided adjacent to the channels downstream of the venturi 64 for releasing a drug or other particle and entraining the drug or other particle in the gas stream. A controller 65 may selectively actuate the release of the particles from the particle-release tape 74.

Figure 7:
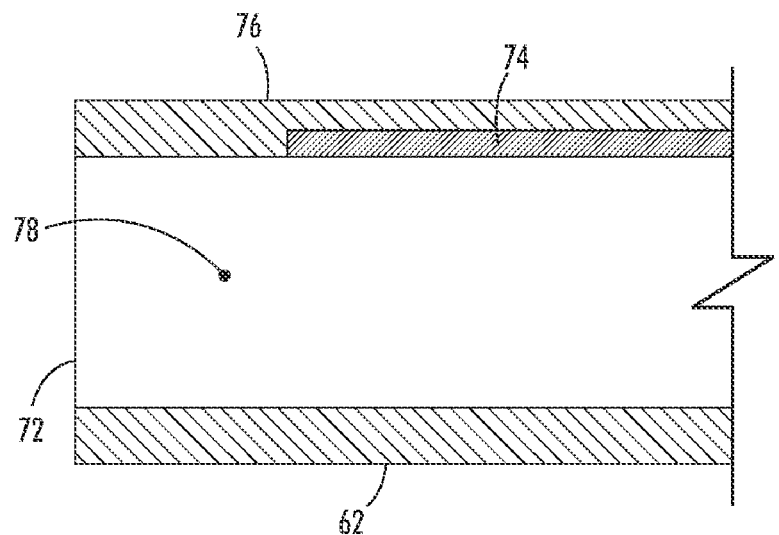
FIG. 7 is a section view, illustrating a drug delivery device including a particle-release tape in accordance with one or more embodiments of the present disclosure.

As illustrated in FIG. 7, the particle-release tape 74 may be positioned within or adjacent to the channel 78 of the collimator 62. In the illustrated embodiment, the particle-release tape 74 is situated within a relief that is etched, cut or milled in a surface of the collimator top plate 76. As such, the particle-release tape 74 faces the channel 78 between the venturi and the outlet 72. When the particle-release tape 74 is actuated to release the particles contained in the particle release tape 74 (e.g., by the application of heat, UV, or electrical energy to the tape), the particles are released into the channel 78 where they are entrained in the gas flowing through the channel 78.

Particles

The device may deliver various types of solid particles and liquids. For example, the device may deliver drugs, tissue abrasive particles, cosmetic particles, nutritional or nourishing particles, or tissue marking particles into the biological tissue.

As used herein, the term "drug" refers to any chemical or biological material or compound suitable for administration by the methods previously known in the art and/or by the methods taught in the present disclosure, that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may be systemic. The drug may be a therapeutic or prophylactic agent. For example, the drug may be a vaccine. The drug may be formulated in a substantially pure form or with one or more excipients known in the art. The excipient material may be homogenously mixed with the drug or heterogenously combined with the drug. For example, the drug may be dispersed in an excipient (matrix) material known in the art, or may be included in a core or coating layer in a multi-layered structure with an excipient material. In some embodiments, the excipient material may function to control in vivo release of the drug, for example to provide timed release (e.g., controlled or sustained release) of the drug.

The device may also contain and deliver tissue abrasive particles. The tissue abrasive particles may be any particles suitable for abrading or penetrating the surface of a biological tissue after delivery from the device and impinging the biological tissue to form, at least transiently, microconduits in the surface of the biological tissue. In one embodiment of the invention, solid, persistent particles that do not dissolve within the tissue after impinging, such as particles comprised of aluminum oxide, also referred to as "alumina," are used to form suitable microconduits. Particles suitable for use in an embodiment include solid phase particles comprised of biocompatible substances that exist in the liquid state at normal physiologic tissue temperatures, for example normal human body temperature. In one embodiment, the particles have a melting point less than about 33° C. For example, the tissue abrasive particles may comprise frozen water. Such solid phase particles impinge onto a localized region of tissue surface, and enter into the tissue, creating microconduits. Such solid phase particles may melt within the tissue, and the resulting liquid may with tissue interstitial fluid.

The device may also contain and deliver nourishing or nutritional particles. The nourishing or nutritional particles may be any particles suitable for promoting or maintaining the viability of the cells of the biological tissue. Such particles may include vitamins, minerals, and other non-drug particles that contain nutrients.

The device may also contain and deliver cosmetic particles. The cosmetic particles may be any particles suitable for providing a cosmetic effect to the biological tissue when delivered to the tissue. For example, the particles may be particles that diminish the appearance of wrinkles, that provide color or alter the coloration of the biological tissue, or that create or reduce localized swelling.

The device may also contain and deliver tissue marking particles. The tissue marking particles may be any particles suitable for marking a tissue for identification, whether such an identification may be made visually, with or without the assistance of technology (e.g., an imaging technology). For example, the particles may comprise an ink or dye or the particles may contain an agent that is visible or capable of imaging with an imaging technology, such as X-Ray, IR, MRI, CT, or ultrasound.

In certain embodiments, the solid particles have a volume average diameter of about 0.1 to about 250 microns. In a preferred embodiment, the solid particles have a volume average diameter equal to or less than ⅕ the width of the conduit or channel, and even more preferably equal to or less than ¹⁄₁₀ the of the width of the conduit or channel.

II. Methods of Administration of Drugs or Other Substances

Methods are provided for the needleless injection of gas streams and drugs or other particles into human or animal tissues. Although many of the examples herein are described in the context of drug delivery into skin, the drug delivery devices disclosed herein may be used to deliver drugs and/or other particles into other tissue surface. For example, the drug delivery device and methods may also be used to deliver drugs into ophthalmic or mucosal tissues. In ophthalmic applications, the velocity of the collimated streams may be controlled to deliver the drugs at a depth sufficient to deliver the drugs into the vitreous humor.

In one aspect, a method is provided for delivering a substance into a human or animal tissue. The method includes delivering a pressurized gas into a collimator to produce a plurality of collimated streams of gas; penetrating the tissue with the plurality of collimated streams of gas to produce a plurality of pores in the tissue; and delivering the substance into the tissue via the plurality of pores. For example, the method may be used to deliver a drug into the tissue. The drug or other substance may be in the form of solid particles having a volume average diameter of about 0.1 to about 250 microns. In a preferred embodiment, the solid particles have a volume average diameter equal to or less than ⅕ the width of the conduit or channel, and even more preferably equal to or less than ¹⁄₁₀ the of the width of the conduit or channel.

The collimator may comprise a plurality of conduits, and the collimated streams of gas may be produced by expanding the pressurized gas through a venturi in each of the plurality of conduits. Each of the plurality of collimated gas streams may have a diameter of a about 5 µm to about 500 µm from the outlet of the conduit. Each of the plurality of collimated streams of gas may have a velocity of about 100 to about 1500 m/s. The pressurized gas may be provided from an on-board gas source. In some embodiments, the gas may be generated on-board.

In some embodiments, the method includes entraining the substance, such as a drug, in each of the plurality of collimated streams of gas. In certain embodiments, the method the plurality of collimated streams of gas are established before the substance is entrained in the plurality of collimated streams of gas. The substance may be entrained in the collimated streams by rupturing a membrane to release the substance into each of the plurality of collimated streams of gas. The entrainment of the substance into the collimated gas stream may occur essentially immediately following generation of the collimated gas stream, or may be occur a short time thereafter, for example, to allow for stabilization of the stream.

Figure 3:
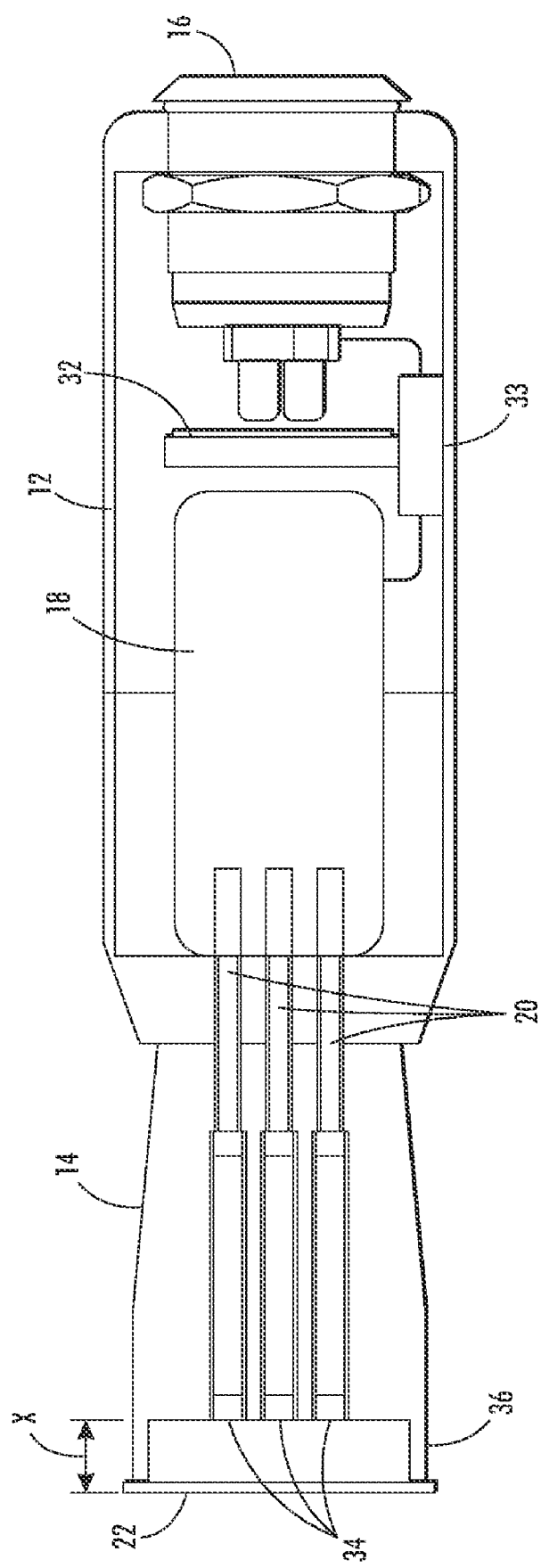
FIG. 3 is a section view, illustrating a drug delivery device in accordance with one or more embodiments of the present disclosure.

To use, the tissue interfacing surface of the device may be placed against a desired tissue surface and then the gas source may be actuated to deliver the pressurized gas to the collimator. For example, the tissue interfacing surface may be placed against the skin or a mucosal surface. Alternatively, in ophthalmic applications, the tissue interfacing surface may be placed against the sclera. The gas source may be actuated by pressing a push switch (such as illustrated in FIG. 3) or another element to initiate the delivery of pressurized gas to the collimator. In certain embodiments, pressing the push switch may also actuate rupturing of a rupturable membrane sealing the drug port.

Figure 8:
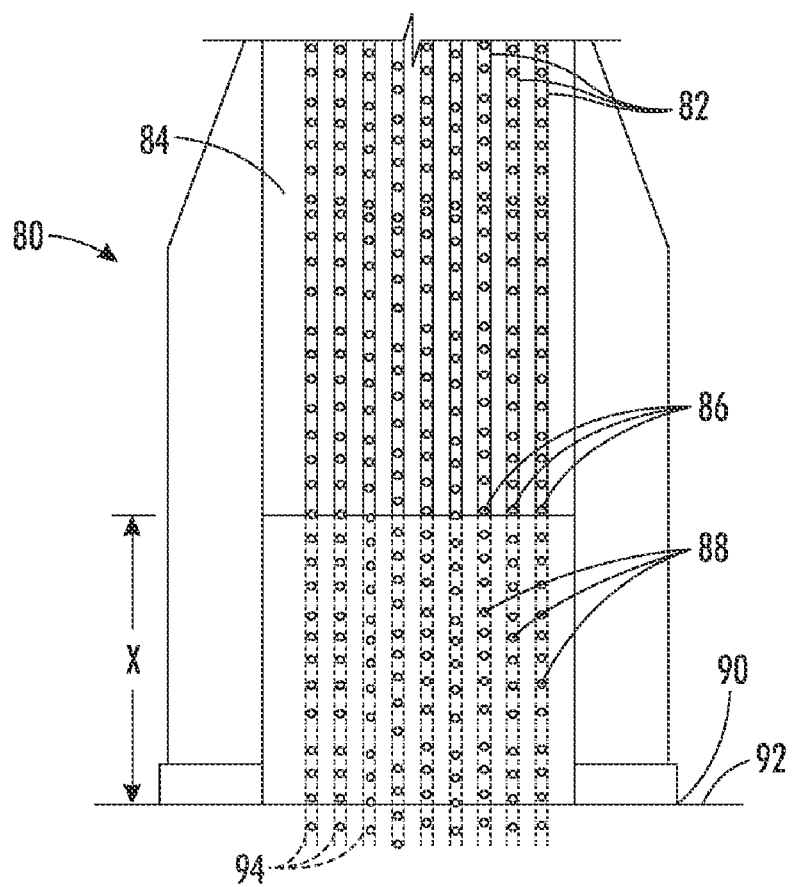
FIG. 8 is a section view, illustrating the delivery of particles in a collimated stream of gas into a tissue in accordance with one or more embodiments of the present disclosure.

As illustrated in FIG. 8, the delivery of a drug or other particles into a tissue may be achieved by forming well-defined collimated streams of particles entrained in a carrier gas 88. The particles, being in well-defined collimated streams, form (at least transiently) microconduits 94 in the tissue 92 upon striking the tissue and pass into the tissue 92 through the formed microconduits 94.

In the illustrated embodiment, the skin-interfacing surface 90 of the device is placed against the tissue 92 (e.g., skin) such that the channels 82 of the collimator 84 are aligned in a substantially perpendicular direction with respect to the tissue 92. The collimator 84 is preferably configured such that the each stream of particles exiting an outlet 86 of the collimator 84 follows a well-defined, collimated path having a width of about 5 µm to about 500 µm between the outlets 86 and the tissue surface 92. Each of the collimated streams of gas (and particles entrained therein) may have a velocity of about 100 to about 1500 m/s. The distance x between the outlets 86 of the collimator 84 and the tissue 92 is preferably between about 0.5 mm and about 10 mm.

The device may also be used to deliver other substances into the tissue. For example, the foregoing devices may contain and be used to deliver poration enhancers, cosmetic particles, nutritional/nourishing particles, and/or marking particles into a tissue.

In some embodiments, the device may deliver substances that enhance poration of the tissue to facilitate the delivery of drugs into the tissue. For example, in any of the aforementioned methods, the device may be used to deliver abrasive particles into a tissue to form, at least transiently, microconduits or pores in the tissue. A drug or other substance may thereafter be delivered into the tissue through the microconduits. In an exemplary embodiment, the device may be used to deliver abrasive particles into the skin to form microconduits in the stratum corneum. A drug-containing delivery system, such as a patch, may then be applied to the tissue site, and the drug may be delivered to the tissue site via the microconduits. Alternatively, the device may be configured to deliver abrasive particles and then another substance, such as a drug, to the tissue in sequence. In such an embodiment, the abrasive particles may be released into the collimator for a first period of time and then the other substance, e.g., the drug, may be released into the collimator for a second, later period of time and pass into the tissue through the microconduits or pores formed by the abrasive particles.

III. Drug Delivery Systems

System for the delivery of drugs and other particles are also disclosed. In one aspect, the system includes a drug delivery device comprising a gas source and one or more cartridge receivers. The system also includes one or more cartridges adapted to insert into the each of the cartridge receiver. Each cartridge includes a collimator and a drug source. The drug source may contain a drug in solid particle or liquid form. The collimator may be adapted to form a plurality of collimated gas streams comprising a drug entrained in a gas when the gas is fed to the collimator from the gas source.

In some embodiments, each cartridge receiver or cartridge further includes a manifold for delivering a gas from the gas source into the collimator. Each collimator may include a plurality of conduits. Each conduit may have an inlet, an outlet, and a venturi between the inlet and the outlet. Each of the conduits may also have an expanding neck region and a drug port between the inlet and outlet downstream of the venturi. The drug port is in fluid communication with the drug source. The drug source may be a drug reservoir containing a drug. In some embodiments, each cartridge may further include a rupturable membrane between the collimator and the drug source. The rupturable membrane seals each of the drug ports.

In some embodiments, the drug delivery device further includes a tissue interfacing surface that is adapted to mate with the desired tissue surface and align first collimator with the tissue such that the conduits are aligned in a direction substantially perpendicular to the tissue when the cartridge is situated in the cartridge receiver. The drug delivery device may further include a standoff between the first collimator and the tissue interfacing surface when the first cartridge is situated in the first cartridge receiver such that a gap is provided between the first collimator and a tissue surface when the tissue interfacing surface is placed against the tissue surface. For example, the standoff may create a gap of about 0.5 mm to about 10 mm The drug delivery device may be configured to produce a plurality of collimated gas streams having a diameter of about 5 µm to about 500 µm at a distance of about 0.5 mm to about 10 mm from the first collimator. In some embodiments, the drug delivery device is configured to produce collimated gas streams having a sufficient velocity to penetrate human stratum corneum.

Figure 5:
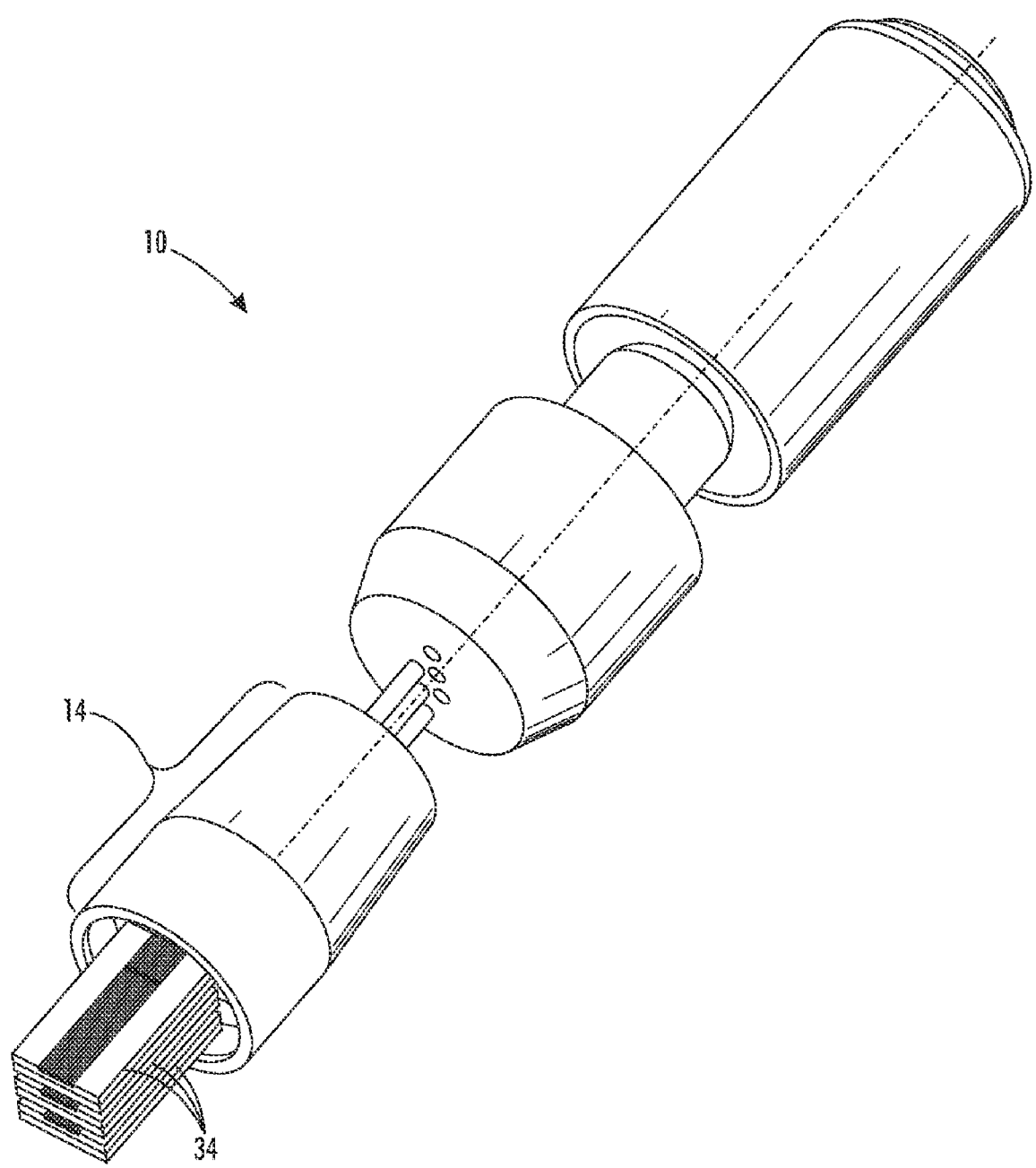
FIG. 5 is an exploded perspective view, illustrating a drug delivery device in accordance with one or more embodiments of the present disclosure.

An exemplary drug delivery system is illustrated in FIG. 5. The system includes a drug delivery device 10 having a cartridge housing 14. The cartridge housing 14 includes three cartridge receivers for receiving three replaceable cartridges 34. The replaceable cartridges 34 may be inserted into the cartridge receivers of the cartridge housing and then may be removed from the cartridge housing after being expended. Although three replaceable cartridges 34 and cartridge receivers are shown, the cartridge housing 14 may be made to accommodate any number of cartridges 34.

Cartridges

As previously described, the drug delivery device may include removable and/or replaceable cartridges that contain the drug or other particles. Each cartridge may contain an amount of a drug sufficient for an individual dosage. Each cartridge may also include a collimator integrally associated therewith.

Figure 4:
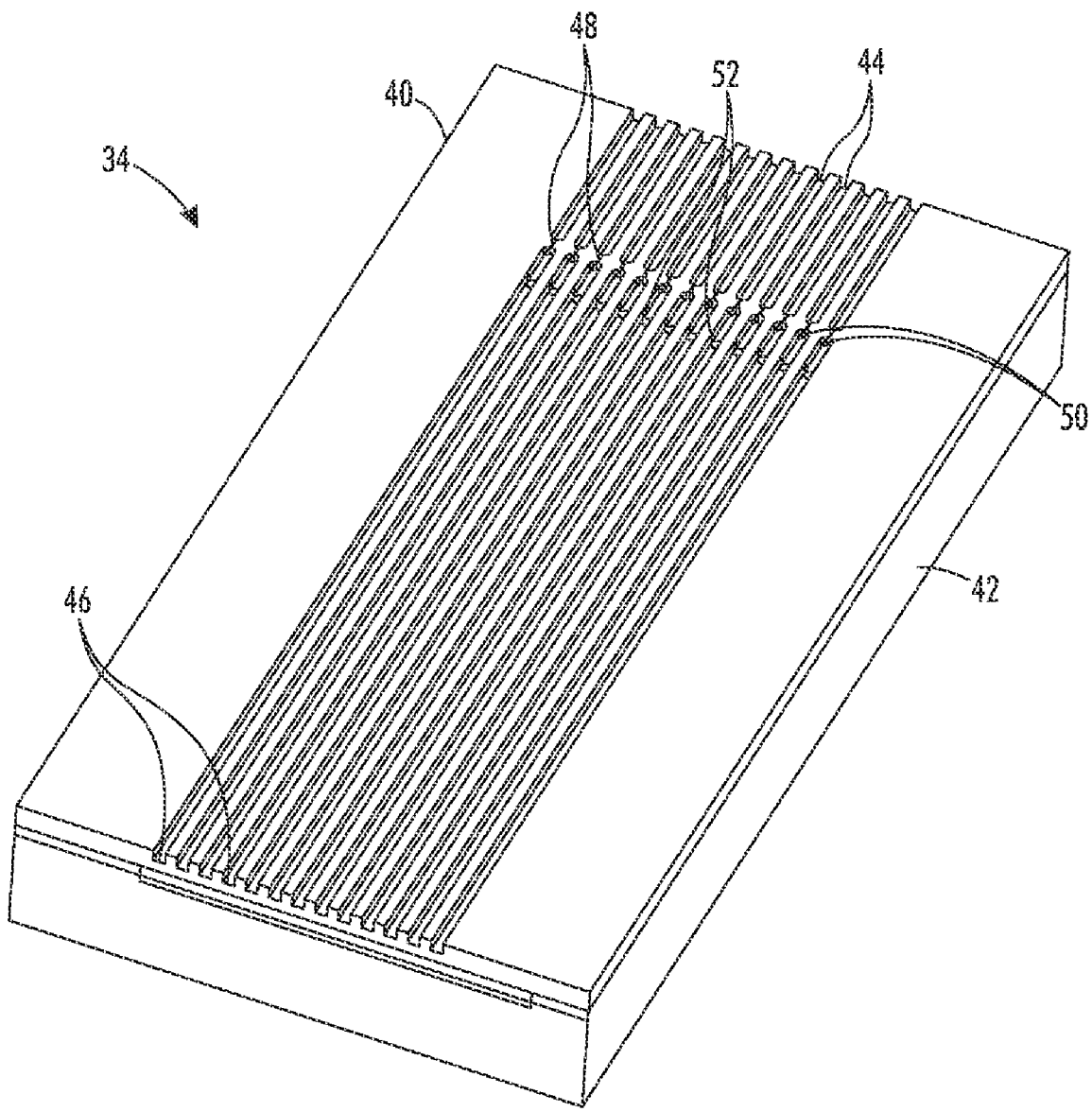
FIG. 4 is a detail view, illustrating a cartridge for a drug delivery device in accordance with one ore more embodiments of the present disclosure.

An exemplary cartridge 34 is illustrated in FIG. 4. In the illustrated embodiment, the collimator 40 is in the form of a plate having a plurality of conduits formed therein. Although not shown, a top plate or other element may be placed over the top of the collimator to seal the open tops of the conduits that are formed in the plate. The collimator 40 is attached to a drug source 42. The drug source 42 may be a reservoir containing a drug in solid particle or liquid form. The conduits of the collimator 40 are fluidly connected with the drug source 42 via drug ports 52 provided in the conduits downstream of the venturis 48.

Another cartridge 60 is illustrated in FIGS. 6-7. In the illustrated embodiment, the collimator 62 is in the form of a plate having a plurality of conduits or channels formed therein. As illustrated in FIG. 7, a collimator top plate 76 may be placed over the top of the collimator 62 to seal the open tops of the conduits that are formed in the plate and to support a particle-release tape 74 that is disposed in a relief of the collimator top plate 76. The particle-release tape 74 therefore faces the channels 78 of the collimator 62.

In some embodiments, the cartridge may contain at least two different substances. Each substance may be delivered into the collimator from a source such as a reservoir or a release-activatable tape. For example, the cartridge may include two or more reservoirs, each containing a different substance. Alternatively, the cartridge may include a release-activatable tape comprising a first substance and a reservoir containing a second substance. The cartridge may be adapted to release each substance independently so that the substances can be delivered at different times, e.g., successively.

In some embodiments, the two or more substances may each be a drug. For example, two or more drugs useful in a combination therapy may be delivered to the tissue. In other embodiments, the cartridge may include abrasive particles and a drug. The cartridge may be adapted to allow for the independent delivery of the abrasive particles and the drug into the collimator so that the abrasive particle may be expelled from the collimator before the drug is delivered.

Patches

In some embodiments, a drug-delivery patch may be used in combination with the device to deliver a drug into the tissue through the microconduits formed in the tissue by the device. The patch may include a drug-permeable tissue-interfacing surface, a drug-impermeable backing layer, and a drug contained between the tissue-interfacing surface and backing layer. The patch may include an adhesive suitable for adhering the patch to the skin. The drug delivery patch may be applied to the tissue site treated with the device so that the drug contained in the patch may diffuse through the drug-permeable tissue-interfacing surface of the patch and into the tissue.

It should be understood that the foregoing relates only to the preferred embodiments of the present application and that numerous changes and modifications may be made herein without departing from the general spirit and scope of the invention as defined by the following claims and the equivalents thereof.

We claim:

1. A delivery device for the delivery of particles into a biological tissue comprising:

a housing;

a gas source comprising a gas or capable of selectively producing a gas;

a first particle source comprising a first plurality of particles;

a first collimator fluidly connected with the gas source and comprising a plurality of conduits adapted to form a first plurality of collimated streams of the first plurality of particles entrained in the gas; and a tissue-interfacing surface located at one end of the housing and adapted to interface with a surface of the tissue and orient the first collimator with the tissue such that the first plurality of collimated streams of the first plurality of particles will penetrate the tissue in a direction substantially perpendicular to the surface of the tissue.

2. The delivery device of claim 1, wherein the first plurality of particles comprise tissue abrasive particles.

3. The delivery device of claim 1, wherein the first plurality of particles comprise tissue marking particles, nourishing particles, nutritional particles, or cosmetic particles.

4. The delivery device of claim 1, wherein the first plurality of particles comprise drug particles.

5. The delivery device of claim 1, further comprising a second particle source comprising a second plurality of particles; and wherein the first collimator is adapted to form a second plurality of collimated streams of the second plurality of particles entrained in the gas.

6. The delivery device of claim 5, wherein the delivery device is adapted to form the second plurality of collimated streams of particles after forming the first plurality of collimated streams of particles.

7. The delivery device of claim 5, wherein the first collimator, the first particle source, and the second particle source are provided in a removable cartridge.

8. The delivery device of claim 1, wherein the first collimator and the first particle source are provided in a removable cartridge.

9. The delivery device of claim 1, wherein the first collimator has an inlet end and an outlet end; and wherein the first particle source is positioned and configured to release the first plurality of particles into the gas between the inlet end and the outlet end of the first collimator.

10. A method of delivering particles into a biological tissue comprising:
   delivering a pressurized gas into a plurality of conduits of a collimator to produce a plurality of streams of gas; and then
   releasing a first plurality of particles into the plurality of streams of gas to produce a plurality of collimated streams of the first plurality of the particles entrained in the gas; and
   delivering the first plurality of particles through a surface of the tissue in a direction substantially perpendicular to the surface of the tissue.

11. The method of claim 10, wherein the first plurality of particles comprise drug particles.

12. The method of claim 10, wherein the first plurality of particles comprise abrasive particles.

13. The method of claim 10, wherein the step of delivering the first plurality of particles through the surface of the tissue forms a plurality of microconduits in the surface of the tissue.

14. The method of claim 13, further comprising:
   applying a drug-delivery patch to the tissue over the plurality of microconduits, the drug-delivery patch comprising a drug; and
   allowing the drug to diffuse into the tissue through the plurality of microconduits.

15. The method of claim 14, wherein the drug-delivery patch comprises a drug-permeable tissue-interfacing surface and a drug-impermeable backing layer, and wherein the drug is contained between the tissue-interfacing surface and the backing layer.

16. The method of claim 10, further comprising, after the step of delivering the first plurality of particles through the surface of the tissue,
   releasing a drug into the plurality of streams of gas to produce a plurality of collimated streams of the drug entrained in the gas; and
   delivering the drug through the surface of the tissue in the direction substantially perpendicular to the surface of the tissue.

17. The method of claim 10, wherein the first plurality of particles are released from a release-activatable tape having the first plurality of particles disposed thereon.

18. The method of claim 10, wherein the step of releasing the first plurality of particles into the plurality of streams of gas comprises rupturing a rupturable membrane separating the first plurality of particles from the collimator.

19. A drug delivery system for delivering a drug into a biological tissue comprising:
   a particle delivery device for the delivery of particles into a tissue comprising:
      a housing;
      a gas source comprising a gas;
      a first particle source comprising a first plurality of particles;
      a first collimator fluidly connected with the gas source and comprising a plurality of conduits adapted to form a first plurality of collimated streams of the first plurality of particles entrained in the gas; and
      a tissue-interfacing surface located at one end of the housing and adapted to interface with a surface of the tissue and align the first collimator with the tissue such that the first plurality of collimated streams of the first plurality of particles will penetrate the tissue in a direction substantially perpendicular to the surface of the tissue; and
   a drug-delivery patch comprising a drug-permeable tissue-interfacing surface, a drug-impermeable backing layer, and a drug contained between the tissue-interfacing surface and the backing layer.

20. The system of claim 19, wherein the first plurality of particles comprise tissue abrasive particles.

* * * * *

UNITED STATES PATENT AND TRADEMARK OFFICE
CERTIFICATE OF CORRECTION

| | | |
|---|---|---|
| PATENT NO. | : 8,388,569 B2 | Page 1 of 1 |
| APPLICATION NO. | : 13/089769 | |
| DATED | : March 5, 2013 | |
| INVENTOR(S) | : Uhland et al. | |

It is certified that error appears in the above-identified patent and that said Letters Patent is hereby corrected as shown below:

On the title page item (73), delete "Xerox Corporation, Norwalk, CT (US)" and insert --Palo Alto Research Center Incorporated, Palo Alto, CA (US)--

Signed and Sealed this
Second Day of July, 2013

Teresa Stanek Rea
*Acting Director of the United States Patent and Trademark Office*